United States Patent [19]

Ruzicka et al.

[11] 3,932,233
[45] Jan. 13, 1976

[54] CALCIUM ELECTRODE AND MEMBRANE AND COMPOSITION FOR USE THEREIN

[75] Inventors: Jaromir Ruzicka, Naerum; Jens Christian Tjell, Virum, both of Denmark

[73] Assignee: Radiometer A/S, Denmark

[22] Filed: Sept. 28, 1973

[21] Appl. No.: 401,809

[30]     Foreign Application Priority Data
    Oct. 2, 1972    United Kingdom............... 45291/72

[52] U.S. Cl. ........ 204/195 M; 204/195 L; 204/296; 252/62.2
[51] Int. Cl.² ................. G01N 27/30; G01N 27/46; C25B 13/08
[58] Field of Search ........... 204/195 L, 195 M, 296, 204/1 T; 252/62.2

[56]         References Cited
         UNITED STATES PATENTS

| | | | |
|---|---|---|---|
| 3,429,785 | 2/1969 | Ross | 204/1 T |
| 3,438,886 | 4/1969 | Ross | 204/195 L |
| 3,445,365 | 5/1969 | Ross | 204/195 L |
| 3,446,726 | 5/1969 | Pungor et al. | 204/195 M X |
| 3,450,631 | 6/1969 | Bloch et al. | 210/22 |
| 3,691,047 | 9/1972 | Ross et al. | 204/195 M |
| 3,729,401 | 4/1973 | Cosgrove et al. | 204/195 L |
| 3,753,887 | 8/1973 | Kedem et al. | 204/195 M |
| 3,767,553 | 10/1973 | Brown et al. | 204/195 M |
| 3,787,309 | 1/1974 | Neti et al. | 204/195 M |

FOREIGN PATENTS OR APPLICATIONS

| | | | |
|---|---|---|---|
| 1,100,186 | 1/1968 | United Kingdom | 204/195 |
| 1,177,406 | 1/1970 | United Kingdom | 204/195 |

*Primary Examiner*—G. L. Kaplan
*Attorney, Agent, or Firm*—Robert E. Burns; Emmanuel J. Lobato; Bruce L. Adams

[57]         ABSTRACT

Calcium di(aryl)phosphates, the aryl groups each carrying at least one carbon chain containing at least 3 carbon atoms, are used as electroactive materials in calcium electrodes. In a preferred calcium electrode, the calcium di(aryl)phosphate is calcium di(p-n-octylphenyl)phosphate which is incorporated in a membrane of polyvinyl chloride plasticized with di(p-n-octyl)-phenylphosphonate.

16 Claims, 3 Drawing Figures

CALCIUM ELECTRODE AND MEMBRANE AND COMPOSITION FOR USE THEREIN

BACKGROUND OF THE INVENTION

1. Field of the Invention

The present invention concerns an electrode for measuring the activity of calcium ions in a solution. The invention also relates to a membrane and a composition for use in such electrode.

2. Prior Art

Calcium electrodes, that is, electrodes used for measuring the concentration or activity of calcium ions in a solution, are known in various embodiments, one of which is described in British Pat. Specification No. 1,107,108. Common to all known calcium electrodes is the fact that they contain an organic ion exchanger, either in solution and mechanically retained within a membrane, or incorporated in a polymer matrix of, e.g., polyvinyl chloride.

Several organic ion exchangers useful in calcium electrodes have been described in the literature: thus, Israelian Pat. No. 26,233 describes the use of thionyl- trifluoroacetone + tributylphosphate of the formula

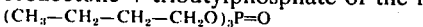

British Pat. Specification No. 1,107,108 describes the use of di(2-ethylhexyl)phosphoric acid of the formula

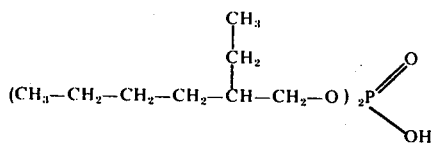

and U.S. Pat. No. 3,445,365 describes the use of di(n-decyl)phosphoric acid of the formula

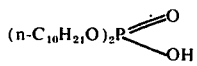

As mentioned above, the ion exchanger — hereinafter called the electroactive material — may be in solution when employed in electrodes. Moreover, the electroactive material is present as wholly or partly converted into its calcium salt. The solvents used are organic solvents and can be of various types. Thus, U.S. Pat. No. 3,429,785 mentions as solvents n-decanol, n-dodecylalcohol, n-decylalcohol and di(n-octyl)-phenylphosphonate of the formula

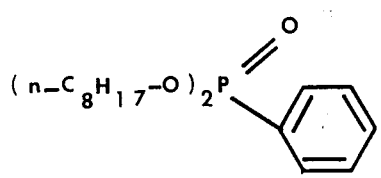

Di(n-octyl)phenylphosphonate belongs to the class of solvents or carriers often called mediators which, through synergetic extraction, have a favourable influence on the quality of the electrodes, resulting inter alia in improved selectivity and a better detection limit.

The above-mentioned electroactive materials used in known calcium electrodes have several disadvantages, viz., low seletivity with regard to the calcium ions over hydrogen ions, sodium ions, potassium ions, etc.

SUMMARY OF THE INVENTION

The present invention provides calcium electrodes which are superior in performance to the above-mentioned known calcium electrodes. The electrodes of the present invention use, as electroactive material, a class of phosphorus compounds not previously suggested for this purpose.

The said phosphorous compounds used as calcium-selective electroactive materials in the electrodes of the present invention are calcium di(aryl)phosphates, the aryl groups of said caclium di(aryl)phosphates each carrying at least one carbon chain containing at least 3 carbon atoms.

Hence, the electroactive materials used according to the invention are calcium salts of organic phosphoric acids containing aryl groups which are bound to phosphorus via oxygen, each of said aryl groups carrying as substitutent at least one carbon chain containing at least 3 carbon atoms. The aryl groups may further contain electrophilic substituents such as nitro, halogen (fluorine, chlorine, bromine, or iodine), or other electrophilic substituents. These organic phosphoric acids are encompassed by the general formula

wherein each aryl group carries at least one carbon chain containing at least 3 carbon atoms, said carbon chain being attached to one of the free positions of the aryl group, and optionally further carries one or more electrophilic substituents such as nitro or halogen.

DETAILED DESCRIPTION OF THE INVENTION

The carbon chain or chains present as substituent on the aryl group is preferably a straight or branched-chain alkyl group, but also alkenyl and alkynyl are contemplated. Preferably, the carbon chain is uninterrupted, but also carbon chains interrupted by oxygen or sulfur atoms are contemplated. Furthermore, if the carbon chain, for example an alkyl group, contains substituents, these are preferably of a character which will not disturb the organophilic character of the carbon chain, such as halogen. It is generally preferred that the carbon chain is an unsubstituted straight or branched-chain alkyl group containing at least three carbon atoms, preferably at least 6 carbon atoms.

Most preferably, the aryl group of the calcium di(aryl)phosphate used according to the invention is an alkylphenyl group, and as examples of specific preferred electroactive materials used according to the invention may be mentioned calcium di(p-n-octyl-phenyl)phosphate, i.e. the calcium salt of di(p-n-octyl-phenyl)phosphoric acid of the formula

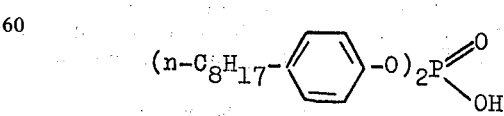

and calcium di[p-(1,1,3,3-tetramethylbutyl)phenyl]-phosphate, i.e. the calcium salt of di[p-(1,1,3,3-tetramethylbutyl)phenyl]phosphoric acid of the formula

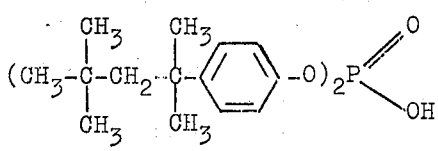

The above-mentioned calcium salts of di(aryl)phosphoric acids used according to the invention may be employed in admixture with the corresponding free di(aryl)phosphoric acids. Indeed, electrodes may be constructed which initially contain, as electroactive material, solely the free di(aryl)phosphoric acid, which will then, during use of the electrode, become more or less saturated with calcium ions. However, it is preferred to load the electrode with the calcium salt of the acid in question already in the production of the electrode.

In the electroactive materials used according to the present invention, the aryl substituents of the phosphoric acid group are believed to give rise to a greater acidity of the phosphoric acid which can be further enhanced with the above-mentioned electrophilic substitution. The carbon chain is believed to increase the organophilicity of the said substances, and hence to increase the distribution coefficient for the substances between organic solvents and water.

The electroactive materials here described can be used in various electrode constructions to produce usable calcium-ion-selective electrodes. Such electrode constructions have been described in various embodiments - e.g., in U.S. Pat. No. 3,445,365 and in British Pat. Specification No. 1,107,108, in Israelian Pat. No. 26,233, as well as by Moody et al., the Analyst, Vol. 95, p. 910 (1970).

The electrodes according to the invention, like the above-mentioned known calcium electrodes, comprise an internal reference system, e.g. a silver/silver halide electrode immersed in an aqeuous electrolyte solution, e.g. pH-buffered calcium chloride solution. The electroactive material is, like in known calcium electrodes, placed in contact with the internal reference system. Various means for positioning the electroactive material in contact with the internal reference system are known, for example porous membranes, one side of which contacts the internal electrolyte solution, the other side of which being contactable with the exterior measured solution, usually an aqueous solution, the pores of the membrane containing the electroactive material, usually dissolved in an organic carrier. It is also known to use e.g. a polyvinyl chloride plasticized with a plasticizer as a non-porous membrane material containing the electroactive material. However, common to all calcium electrodes, including the constructions specifically referred to above, is that they comprise 1. an internal reference system, and
2. an electroactive material sensitive to calcium ions, said electroactive material being positioned in the electrode so as to be contactable with the measured solution and to be in electrical contact with said internal reference system.

Hence, the electrode according to the present invention can be characterized as an electrode for measuring the activity of calcium ions in solution, comprising 1. an internal reference system, and
2. a calcium di(aryl)phosphate, said calcium di(aryl)phosphate being positioned in the electrode so as to be contactable with said measured solution and to be in electrical contact with said internal reference system, the aryl groups of said calcium di(aryl)phosphate each carrying at least one carbon chain containing at least 3 carbon atoms. Details concerning the substitution of the aryl groups and the preferred substituted aryl groups are given above.

As mentioned above, the calcium di(aryl)phosphate may be present in admixture with the corresponding di(aryl)phosphoric acid.

In the electrodes according to the invention, the calcium di(aryl)phosphate is preferably employed incorporated in an organic carrier. The organic carrier may be a solvent for the calcium di(aryl)phosphate (and for the corresponding di(aryl)phosphoric acid if present), for example one of the solvents mentioned in U.S. Pat. No. 3,429,785 referred to above. Especially preferred organic carriers for the calcium di(aryl)phosphates are "mediators" such as di(alkyl)arylphosphonates, and in preferred electrodes according to the invention, the calcium di(aryl)phosphate employed is incorporated in a di(alkyl)arylphosphonate. Preferably, the di(alkyl)arylphosphonate is a di(alkyl)phenylphosphonate, and as a specific preferred example thereof may be mentioned di(n-octyl)phenylphosphonate, the formula of which is given above.

When a porous membrane or a porous body is used in the electrodes according to the invention as means for containing the calcium di(aryl)phosphate in electrical contact with the internal reference and contactable with the measured solution, it is preferred to use the calcium di(aryl)phosphate dissolved in a di(alkyl)arylphophonate, e.g. di(n-octyl)phenylphosphonate. One aspect of the invention comprises, as a novel composition for use in an electrode according to the invention, a calcium di(aryl)phosphate as defined above dissolved in a di(alkyl)arylphosphonate. A preferred composition of this kind comprises calcium di(p-n-octylphenyl)phosphate dissolved in di(n-octyl)phenylphosphonate. Usually, it is preferred that the weight ratio between calcium di(aryl)phosphate and the di(alkyl)arylphosphonate is between 1:5 and 1:50.

The above-mentioned composition according to the invention may be incorporated in electrodes according to the invention during their production, but may also be sold per se for use as a suitable form of electroactive material to be employed in existing electrode structures designed for known types of e.g. calciumsensitive electroactive materials.

In an especially preferred embodiment of the electrode according to the invention, the organic carrier for the calcium di(aryl)phosphate is a plastic plasticized with an organic plasticizer such as an ester, usually an alkyl ester, of an organic or inorganic acid, e.g. dioctylphthalate, diotyladipate, dioctylsebacate, trioctylphosphate, tributylphosphate or, preferably a di(alkyl)arylphosphonate. In practice, the plastic plasticized with the plasticizer and acting as a carrier for the electroactive material will usually be in the form of a membrane positioned in contact with the electrolyte of the internal reference system. A suitable plastic for use in such non-porous membrane is polyvinyl chloride, and a preferred plasticizer-mediator is di(n-octyl)phenylphosphonate.

One aspect of the invention relates to such a membrane comprising a calcium di(aryl)phosphate incorporated in a plastic plasticized with an organic plasticizer, e.g. of the type stated above, preferably a di(alkyl)arylphosphonate. Such membranes may be used in the electrodes according to the invention, or they may be sold per se for the replacement of conventional membranes in existing membrane electrode constructions.

Membranes according to the invention may be prepared by dissolving the plastic, the di(alkyl)arylphosphonate and the calcium di(aryl)phosphate in an organic solvent such as tetrahydrofuran, casting the solution, for example in small rings positioned on a glass plate, and allowing the solvent to evaporate. If desired, the membrane structure may be reinforced by incorporation of e.g. a nylon network, e.g. by placing the nylon network on the glass plate before or during casting, or by first casting one layer of the membrane, allowing the solvent to evaporate partially or completely, placing the nylon network on the resulting solidified structure, and thereafter performing a second casting operation. The weight ratio between the electroactive calcium di(aryl)phosphate and the plasticizer, preferably the di(alkyl)arylphosphonate, in the said membranes is preferably between 1:5 and 1:50, and the weight ratio between the plasticizer, preferably the di(alkyl)arylphosphonate, and the plastic, preferably the polyvinyl chloride, is usually between 3:1 and 1:10, preferably between 2.5:1 and 1.5:1.

In comparison with known calcium electrodes, the electrodes according to the invention and the electrodes preparable by means of the compositions or the membranes of the invention offer the advantages of improved selectivity with respect to calcium ions relative to hydrogen ions and other interfering ion species, and lower detection limit.

The calcium di(aryl)phosphates used according to the present invention or the corresponding phosphoric acids are known compounds or may be prepared in accordance with or in analogy to known methods. Thus, for example, di[p-(1,1,3,3-tetramethylbutyl)-phenyl]phosphoric acid is described by D. F. Peppard, G. W. Mason, W. J. Driscoll, and R. J. Sironin in J. Inorg. Nuclear Chem., vol. 7, p. 276 (1968). A general synthesis for the di(aryl)phosphoric acids contemplated here comprises reacting phosphorus oxychloride with the phenol corresponding to the desired substituted aryl group in the presence of a base such as pyridine. The calcium salt of the acid may suitably be prepared by precipitation with calcium ions from a methanol solution.

BRIEF DESCRIPTION OF THE DRAWINGS

FIGS. 2 and 3 will be further discussed in connection with the examples.

DETAILED DESCRIPTION OF FIG. 1

Figure 1:
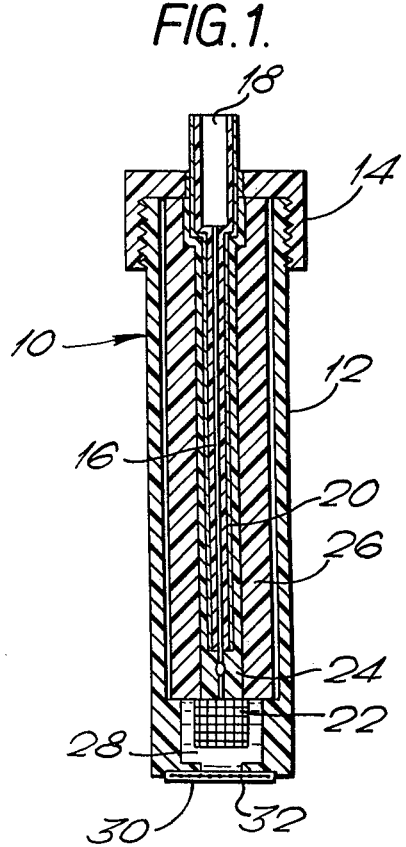
FIG. 1 is a diagrammatic sectional representation of an electrode of the invention.

A calcium-sensitive electrode 10 according to the present invention comprises electrically-insulating container means such as a tube 12 of an inert material, for example glass or an organic polymer such as polyvinyl chloride. The tube may be capped by a lid 14 of inert material which acts as a closure and as a support for an electrically conductive lead 16 having at the upper end thereof a connection part 18 for connection with a potential measuring apparatus, e.g. via conventional wiring. The lead is shielded by a shield 20 and is connected to an Ag/AgCl electrode 22. In order to obtain a rugged construction, the shielded lead may be encapsulated in an epoxy resin body 24, as shown, and further surrounded by a polytetraflouroethylene tube 26, as shown. The Ag/AgCl electrode contacts an aqueous electrolyte 28, e.g. a $10^{-2}M$ $CaCl_2$ solution in pH-buffer. A membrane 30 comprising electroactive substance incorporated in a plasticized plastic, for example calcium di(p-n-octylphenyl)phosphate incorporated in polyvinyl chloride plasticized with di(n-octyl)phenylphosphonate, and optionally reinforced with e.g. a network 32 of an inert material such as plastic, e.g. nylon is attached to the end of the tube 12, for example by means of tetrahydrofuran when the tube 12 is a polyvinyl chloride tube. The membrane 30 may also be tightly attached to the tube 12 by means of a cap (not shown) or any other suitable means ensuring liquid-tight connection between the membrane and the tube and permitting contact between the lower surface of the membrane and an exterior solution.

The electrode shown in FIG. 1 is employed by contacting the exterior surface of the membrane 30 with the sample solution. The potential generated is measured by means of otherwise conventional equipment for potentiometric measurement, including a reference electrode communicating with the sample solution and a potential measuring apparatus connected to the reference electrodes and to the connection 18 of the lead 16.

EXAMPLE 1

Preparation of Calcium Di(p-octylphenyl)phosphate

Dry pyridine (79 g, 1 mole) and phosphorus oxychloride (30.6 g, 0.2 mole) were dissolved in 75 ml of ether. A solution of 106.0 g of p-n-octylphenol was added dropwise under reflux and vigorous agitation; a white precipitate of pyridinium chloride was formed. After the addition, the mixture was refluxed for additionally 1.5 hours, whereafter water and subsequently concentrated hydrochloric acid were added. The ether phase was separated, washed twice with 1 M hydrochloric acid and evaporated in vacuum. The residue was a viscous oil, which was purified in the following manner:

50 g of the product were dissolved in 1500 ml of pure methanol, and 0.15 mole of $CaCl_2$ in 60 ml of water was added. NaOH (33%) was added to pH 10. The resulting white precipitate was separated by filtration and slurried in 1 liter of water and 100 ml of concentrated hydrochloric acid. 150 ml of ether was added, and the ether phase was separated and evaporated in vacuum at 80°C until 1 mm Hg. The product crystallized.

The crystallic acid was converted into the calcium salt in the following manner: 10 g of the product (0.02 mole) were dissolved in 1 liter of pure methanol. Saturated $Ca(OH)_2$ solution was added to pH 8 (about 500 ml). The resulting calcium salt was a white precipitate which was separated by filtration, washed with methanol and water and dried in vacuum.

EXAMPLE 2

Preparation of a Solution of Calcium Di(p-n-octylphenyl)phosphate in Di(n-octyl)phenylphosphonate To 100 g of di(n-octyl)phenylphosphonate in a 250 ml flask were added 10 g of calcium di(p-n-octylphenyl)phosphate. The flask was shaken until a clear solution was obtained.

EXAMPLE 3

Preparation of Membranes

Polyvinyl chloride (Breon S 110/10, BP Chemicals International Ltd.) (0.2400 g) was dissolved in 18 ml of distilled tetrahydrofuran, and the solution was added to a solution of 0.0620 g of calcium di(p-n-octylphenyl)-phosphate in 0.54 g of di(n-octyl)phenylphosphonate. The mixture was shaken until homogeneous.

Ground plane glass rings (diameter 30 mm) were placed on a plane glass plate, and 6 ml of the mixture prepared as described above were placed in each ring and covered with filter paper. A temperature of about 32°C was maintained for 1 – 2 days, and the tetrahydrofuran evaporated through the filter paper. The resulting membranes were removed from the glass plate.

EXAMPLE 4

Comparison between Electrode According to the Invention and Known Calcium Electrode The known electrode was calcium electrode type 92-20 from Orion Research Inc., Mass., USA. The construction of this electrode is as described in British Patent Specification No. 1,107,108 and comprises a reservoir containing a solution of calcium di(n-decyl)-phosphate in di(n-octyl)phenylphosphonate and a porous membrane loaded with said solution and communicating at its rim with said reservoir, the upper surface of the membrane center part being in contact with an internal reference system and the lower surface thereof being exposed for contact with a sample solution.

The electrode according to the invention was established in the same type of structure as the above-mentioned known electrode, but using the calcium di(p-n-octylphenyl)phosphate solution prepared according to Example 2 instead of the known calcium di(n-decyl)-phosphate solution in the membrane and the reservoir.

Using a standard calomel electrode as a reference, both electrodes were used for potentiometric measurements at varying pH values in the following solutions:
1. $10^{-2}$ M $Ca^{++}$ solution
2. $10^{-3}$ M $Ca^{++}$ solution
3. $10^{-4}$ M $Ca^{++}$ solution
4. $10^{-3}$ M CaEDTA + $10^{-3}$ M EDTA + $10^{-1}$ M NaCl
5. $10^{-3}$ M CaEDTA + $10^{-3}$ M EDTA + $5 . 10^{-3}$ M NaCl The pH adjustment was performed by adding hydrochloric acid or sodium hydroxide.

Figure 2:
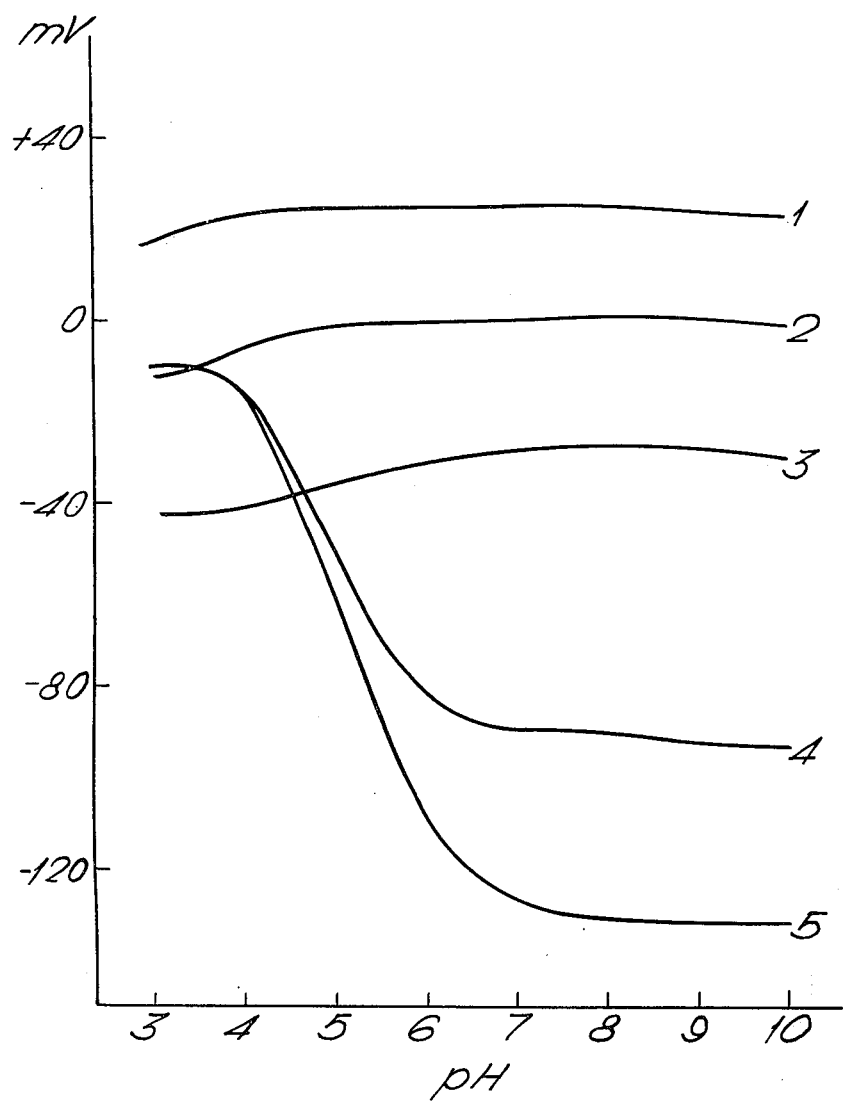
FIGS. 2 and 3 are graphical representations showing the response, in term of potential, of an electrode according to the invention (FIG. 2) and a known calcium electrode (FIG. 3), respectively, in various solutions at varying pH.
Figure 3:
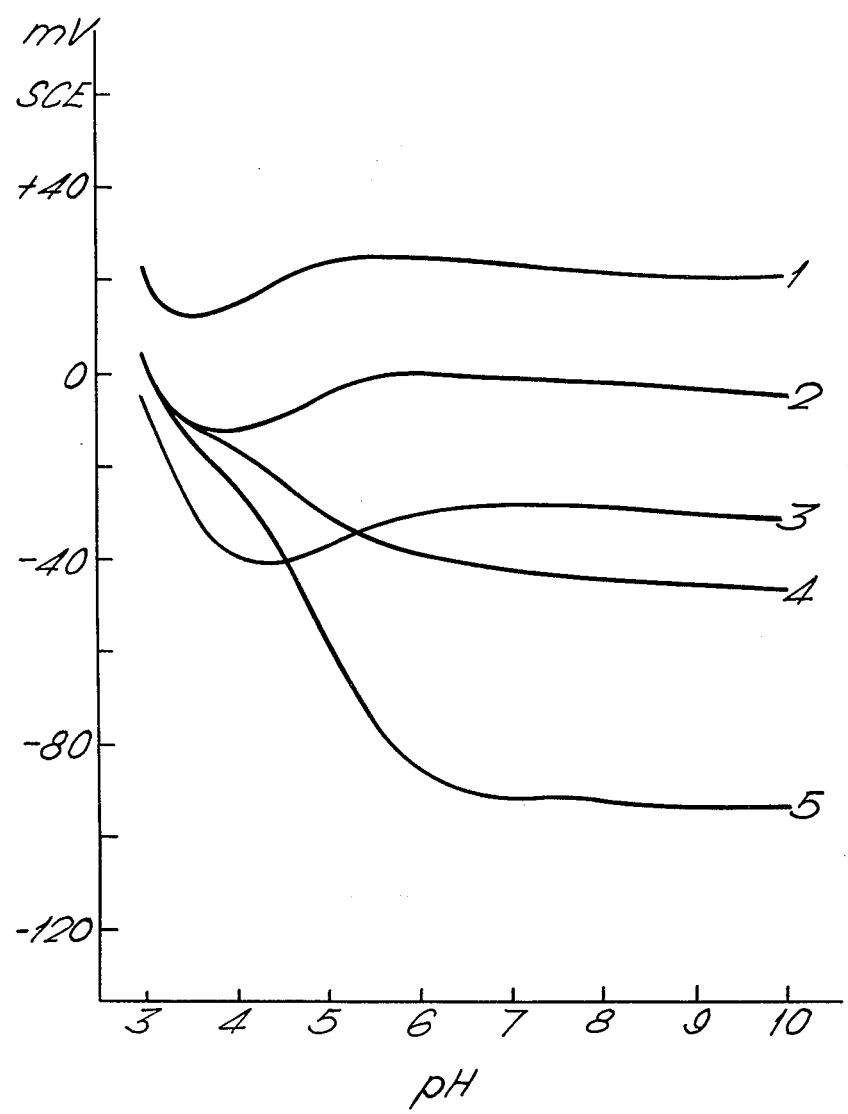

The electrode responses in mV appear from FIG. 2 (electrode according to the invention) and FIG. 3 (the known calcium electrode). It will be noted that the electrode according to the invention shows better performance at low pH values (less dip), which means that it can be used at lower pH value than the known electrode. Furthermore, it is evident that the selectivity of the electrode according to the invention towards the sodium ion is approximately 100 times better than the selectivity of the known electrode, and that the detection limit of the electrode according to the invention is at least 20 times lower than the detection limit of the known electrode.

Similar measurements carried out with electrodes according to the invention and constructed as shown in FIG. 1 gave similar excellent results, and it may be concluded that the specific construction of the electrode according to the invention has little or no influence on the improvement obtained through the present invention.

We claim:
1. An electrode for measuring the activity of calcium ions in a solution, comprising
    1. an internal reference system, and
    2. a calcium di(aryl)phosphate, said calcium di(aryl)phosphate being positioned in the electrode so as to be contactable with said measured solution and to be in electrical contact with said internal reference system, the aryl groups of said calcium di(aryl)phosphate each carrying at least one carbon chain containing at least three carbon atoms, the aryl groups of said calcium di(aryl)phosphate further carry electrophilic substitution, and the electrophilic substitution is nitro or halogen substitution.
2. An electrode for measuring the activity of calcium ions in a solution, comprising:
    a. an internal reference system, and
    b. calcium di(p-n-octylphenyl)phosphate, said calcium di(p-n-octylphenyl)phosphate being positioned in the electrode so as to be contactable with said measured solution and to be in electrical contact with said internal reference system.
3. An electrode as claimed in claim 2, wherein the calcium di(p-n-octylphenyl)phosphate is incorporated in an organic carrier.
4. An electrode as claimed in claim 3, wherein the organic carrier is a plastic plasticized with an organic plasticizer.
5. An electrode as claimed in claim 4, wherein the plastic is polyvinyl chloride.
6. An electrode as claimed in claim 5, wherein the plasticizer is a di(alkyl)arylphosphonate.
7. An electrode as claimed in claim 6, wherein the di(alkyl)arylphosphonate is di(n-octyl)phenylphosphonate.
8. An electrode as claimed in claim 3, wherein the organic carrier is a di(alkyl)arylphosphonate.
9. An electrode as claimed in claim 2, wherein the phenyl groups of said calcium di(p-n-octylphenyl)-phosphate further carry nitro or halogen substitution.
10. An electrode as claimed in claim 2, wherein the calcium di(p-n-octylphenyl)phosphate is present in admixture with the corresponding di(p-n-octylphenyl) phosphoric acid.
11. A membrane for use in an electrode as claimed in claim 4, comprising calcium di(p-n-octylphenyl)phosphate incorporated in a plastic plasticized with an organic plasticizer.
12. A membrane as claimed in claim 11, wherein the plastic is polyvinyl chloride.
13. A membrane as claimed in claim 12, wherein the plasticizer is a di(alkyl)arylphosphonate.
14. A membrane as claimed in claim 13, comprising calcium di(p-n-octylphenyl)phosphate incorporated in polyvinyl chloride plasticized with di(n-octyl)phenylphosphonate.
15. A composition for use in an electrode as claimed in claim 2, comprising calcium di(p-n-octylphenyl)-phosphate dissolved in a di(alkyl)arylphosphonate.
16. A composition as claimed in claim 15, wherein the di(alkyl)arylphosphonate is di(n-octyl)phenylphosphonate.

* * * * *